(12) United States Patent
Corbucci et al.

(10) Patent No.: US 8,688,201 B2
(45) Date of Patent: Apr. 1, 2014

(54) SYSTEM AND METHOD TO MONITOR EJECTION TIME AND QT INTERVAL TO ALERT PATIENTS BEFORE SYNCOPAL EVENTS

(75) Inventors: Giorgio Corbucci, Cento (IT); Willem Boute, Brummen (NL); Patrick Scholten, Lettele (NL); Josephus P. A. Smit, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 1525 days.

(21) Appl. No.: 12/108,745

(22) Filed: Apr. 24, 2008

(65) Prior Publication Data

US 2009/0270748 A1    Oct. 29, 2009

(51) Int. Cl.
*A61N 1/37* (2006.01)
(52) U.S. Cl.
USPC .......................................................... 600/513
(58) Field of Classification Search
USPC .................... 600/373, 374, 508, 509, 513
See application file for complete search history.

(56) References Cited

U.S. PATENT DOCUMENTS

| | | | |
|---|---|---|---|
| 5,549,650 A * | 8/1996 | Bornzin et al. .................. | 607/24 |
| 5,593,431 A | 1/1997 | Sheldon | |
| 6,219,579 B1 * | 4/2001 | Bakels et al. .................... | 607/17 |
| 6,719,701 B2 | 4/2004 | Lade | |
| 6,788,970 B1 * | 9/2004 | Park et al. ......................... | 607/17 |
| 6,792,308 B2 * | 9/2004 | Corbucci ......................... | 607/17 |
| 6,836,682 B2 | 12/2004 | van Dam | |
| 6,959,214 B2 | 10/2005 | Pape et al. | |
| 7,715,909 B2 * | 5/2010 | Zanetti et al. .................. | 600/523 |
| 7,742,815 B2 * | 6/2010 | Salo et al. ......................... | 607/23 |
| 8,282,568 B2 * | 10/2012 | Elle et al. ....................... | 600/508 |
| 2003/0100925 A1 * | 5/2003 | Pape et al. ........................ | 607/17 |
| 2005/0131470 A1 | 6/2005 | Vitali et al. | |
| 2005/0267381 A1 * | 12/2005 | Benditt et al. ................. | 600/547 |
| 2007/0060959 A1 | 3/2007 | Salo et al. | |
| 2008/0033490 A1 | 2/2008 | Giftakis et al. | |
| 2008/0255464 A1 * | 10/2008 | Vincent .......................... | 600/514 |
| 2009/0030471 A1 * | 1/2009 | Rousso et al. ................... | 607/27 |

FOREIGN PATENT DOCUMENTS

EP          1331022          7/2003

OTHER PUBLICATIONS

Petridei et al., "A Swim-test and Echocardiographic Results on Male Junior Water Polo Player's", Facta Universitatis Series Physical Education and Sport, vol. 1, No. 10, 2003, pp. 1-10.*
International Search Report, PCT/US2009/040414, 6 pages.

* cited by examiner

*Primary Examiner* — Christopher D Koharski
*Assistant Examiner* — Frances Oropeza
(74) *Attorney, Agent, or Firm* — reed A. Duthler; Stephen W. Bauer (57) ABSTRACT

An implantable medical device and associated method predict syncope based on detecting a change in ejection time. A physiological signal is sensed that is responsive to mechanical changes associated with the cardiac ejection phase. A time interval corresponding to cardiac ejection time is detected from the physiological signal. A sudden change in the time interval is used as a predictor of syncope and causes a patient alert to be generated in response to the detected change.

23 Claims, 11 Drawing Sheets

SYSTEM AND METHOD TO MONITOR EJECTION TIME AND QT INTERVAL TO ALERT PATIENTS BEFORE SYNCOPAL EVENTS

TECHNICAL FIELD

The disclosure relates generally to implantable medical devices and, in particular, to an implantable device and associated methods for predicting syncope.

BACKGROUND

Syncope is typically preceded by a sudden drop in heart rate, blood pressure or both. Without warning to the patient, a syncopal episode can pose considerable risk of injury to the patient, particularly if the patient is standing or driving a car at the time of syncope. Accordingly, it is desirable to provide the patient with some warning that syncope is likely to occur so that the patient has time to sit down, park a car, or take other actions such as specific counter-maneuvers to reduce the risk of injury and/or prevent syncope. Implantable devices that include transvenous intracardiac leads can measure heart rate and blood pressure for use in predicting syncope. However such leads are invasive and may not be required for other therapeutic or monitoring reasons in a particular patient

DETAILED DESCRIPTION

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
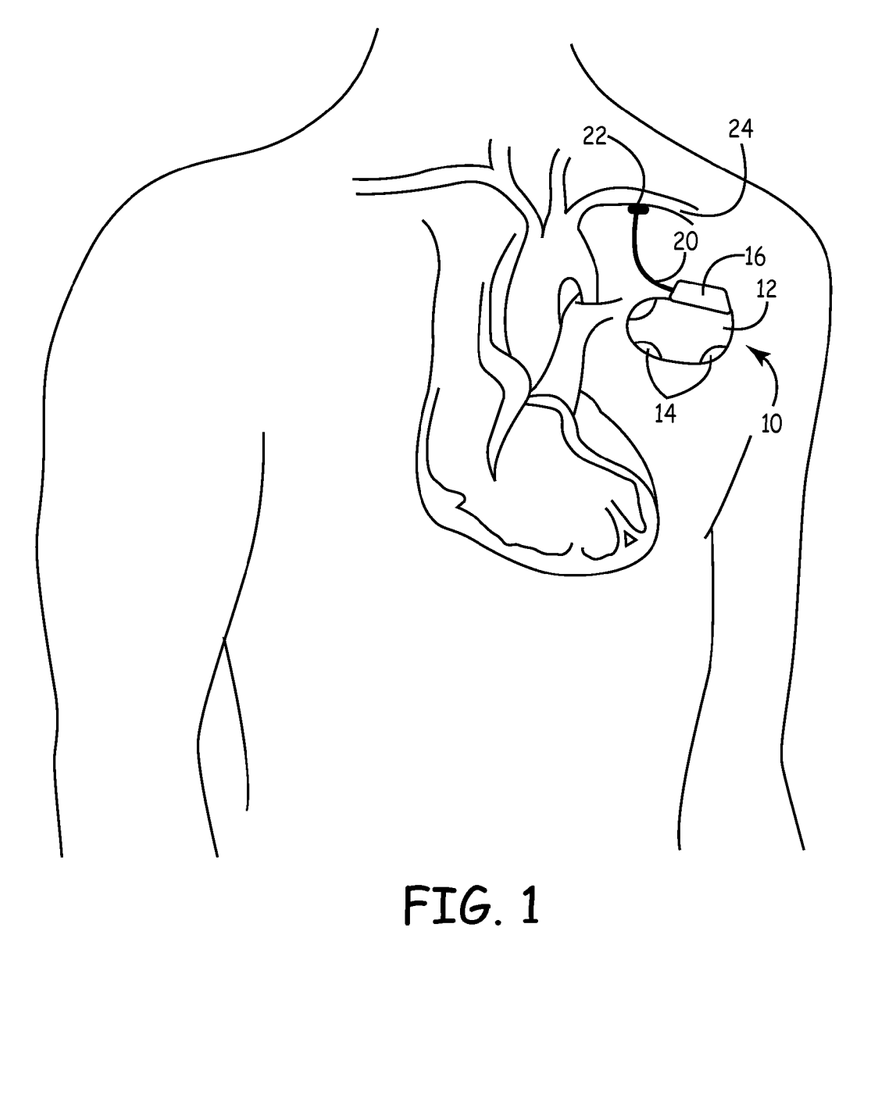
FIG. 1 is a schematic diagram of an implantable medical device (IMD) in communication with a sensor for use in predicting syncope.

FIG. 1 is a schematic diagram of an implantable medical device (IMD) in communication with a sensor for use in predicting syncope. IMD 10 is a subcutaneously or submuscularly implanted device capable of monitoring physiological signals for use in detecting or diagnosing a patient condition. IMD 10 is configured to generate an alert or warning to the patient upon detecting an alert condition. In particular, IMD 10 is configured to detect physiological signals corresponding to an impending syncopal episode and generate a patient alert to warn the patient of the impending syncope. The patient may then respond to the warning by taking safety precautions or performing preventative maneuvers. IMD 10 may additionally include therapy delivery capabilities, such as drug delivery or electrical stimulation therapies, which may be delivered or adjusted in response to a syncope prediction.

IMD 10 is shown as part of a subcutaneous system and is not coupled to transvenous or intrathoracic implanted leads, electrodes or other sensors. IMD 10 includes electrodes 14 incorporated on the housing 12 of IMD 10 for sensing subcutaneous ECG signals. One or more electrodes 14 may be implemented along the IMD housing 12 in a variety of sensing configurations. IMD 10 is coupled to a subcutaneous lead 20 extending from an IMD connector block 16 and carrying a sensor 22. Lead 20 is tunneled subcutaneously or submuscularly to deploy sensor 22 at an implant site corresponding to an artery for sensing an arterial pulse signal. In FIG. 1, sensor 22 is embodied as an accelerometer positioned along the left subclavian artery 24. Sensor 22 is a sensor responsive to the arterial pulse and in particular responsive to the pulsatile motion of the subclavian artery wall. In alternative embodiments, sensor 22 may be positioned in operative relation to other arteries, such as a carotid artery, femoral artery, brachial artery, or any other peripheral artery or branch.

IMD 10 is shown implanted in a pectoral location but may be implanted subcutaneously or submuscularly in any desired location relative to the implant site of sensor 22 that allows communication between sensor 22 and IMD 10. Sensor 22 may be coupled to IMD 10 via a lead 20 for electrically coupling sensor 22 to IMD 10 and transferring sensor signals to circuitry enclosed in housing 12. In alternative embodiments, sensor 22 may be embodied as a "leadless" sensor having its own power supply and telemetry circuitry for transmitting signals, for example RF signals, to IMD 10 wirelessly. Alternatively sensor 22 may be incorporated along housing 12, internal or external to housing 12, with IMD 10 implanted at a location that allows sensor 22 to sense an arterial pulse signal, e.g. in close proximity or against an artery.

Sensor 22 may be embodied as any sensor responsive to an arterial pulse. "Arterial pulse" as used herein refers to either the pulsatile flow within the artery or the resulting pulsatile motion of the arterial wall. As such, sensor 22 may be a motion sensor such as an accelerometer as discussed above, for detecting pulsatile arterial wall motion. Alternatively, sensor 22 may be embodied as a flow sensor for sensing the velocity or acceleration of blood flow within the artery or an impedance sensor for sensing changes in the volume of blood in a portion of the artery. As will be described herein, the signal responsive to the arterial pulse is used for determining a time interval corresponding to cardiac ejection time in one embodiment of the invention. Embodiments utilizing a sensor placed along a peripheral artery for sensing the pulsatile arterial signal avoid the need for placing transvenous leads, as normally required by methods relying on blood pressure signals for predicting syncope.

The onset of cardiac ejection corresponds to the opening of the aortic valve and the end of cardiac ejection occurs upon closure of the aortic valve. The term "ejection time" therefore refers to the time interval that blood is being ejected from the left ventricle, while the aortic valve is open. Cardiac ejection time can rapidly shorten or lengthen prior to syncope. In neurologically-mediated syncope, a sudden drop in blood pressure results in reduced ventricular filling which in turn causes the observed sudden decrease in ejection time.

On the other hand, in the case of progressive bradycardia precipitating a syncope event, the ejection time suddenly increases. This sudden increase in ejection time occurs disproportionately with the QT interval early after the heart rate decrease. Ejection time changes immediately with a rapid change in heart rate because it reflects the mechanical behavior of the heart while the QT interval changes more slowly than ejection time and heart rate. In response to a physiological change in heart rate, the QT interval will change proportionally and the ejection time will shorten or lengthen in a physiological way that is substantially proportional to the change in QT interval. As such, a sudden change in ejection time, particularly a sudden change in ejection time that is not accompanied by a corresponding sudden change in QT interval, can be used as a predictor of syncope. A "sudden" or "rapid" change in ejection time is used herein to refer to a change in ejection time that occurs within about 20 to 120 seconds. The change in ejection time that occurs prior to syncope is normally a decrease or increase of at least about 10% in ejection time. As such, a sudden change in ejection time that is predictive of syncope is a change of about 10% in less than about 2 minutes in one embodiment of the invention.

Sensor 22 is therefore any sensor that can be used for determining a time interval that is substantially equal to or proportional to the cardiac ejection time. In general this includes any sensor responsive to the pulsatile motion of the arterial wall and/or the pulsatility of blood flow within the artery since this pulsatility corresponds to the ejection of blood during a given heartbeat, after aortic valve opening up to aortic valve closure. The pulsatile signal corresponding to an arterial pulse will typically be delayed in time relative to actual ejection time of the heart depending on the position of the sensor. For example, the pulse wave will arrive later at a more distal artery, such as the femoral artery, than at an artery more proximal to the heart, such as a subclavian or carotid artery. Nonetheless, a time interval can be derived from the arterial pulsatile signal that is proportional to the actual cardiac ejection time.

While an accelerometer is one useful sensor for detecting pulsatile arterial wall motion for deriving a time interval corresponding to the cardiac ejection time, other sensor signals are contemplated. For example, an acoustical sensor may be used to detect the first heart sound corresponding to aortic valve opening and the onset of the ejection phase and the second heart sound corresponding to aortic valve closure and the end of the ejection phase. An impedance sensor could be used to detect changes in a heart chamber volume or a blood vessel volume for detecting the maximum and/or minimum volumes associated with the start and/or end of ejection. Thus, in a broader sense, sensor 22 is any sensor responsive to mechanical events, which may include pressure, flow, volume changes, tissue motion, or acoustical events associated with the start and end of the cardiac ejection phase and may be located within or one IMD housing 12, carried by a lead, or leadless sensors having their own power supply and telemetry circuitry in communication with an IMD.

Figure 2:
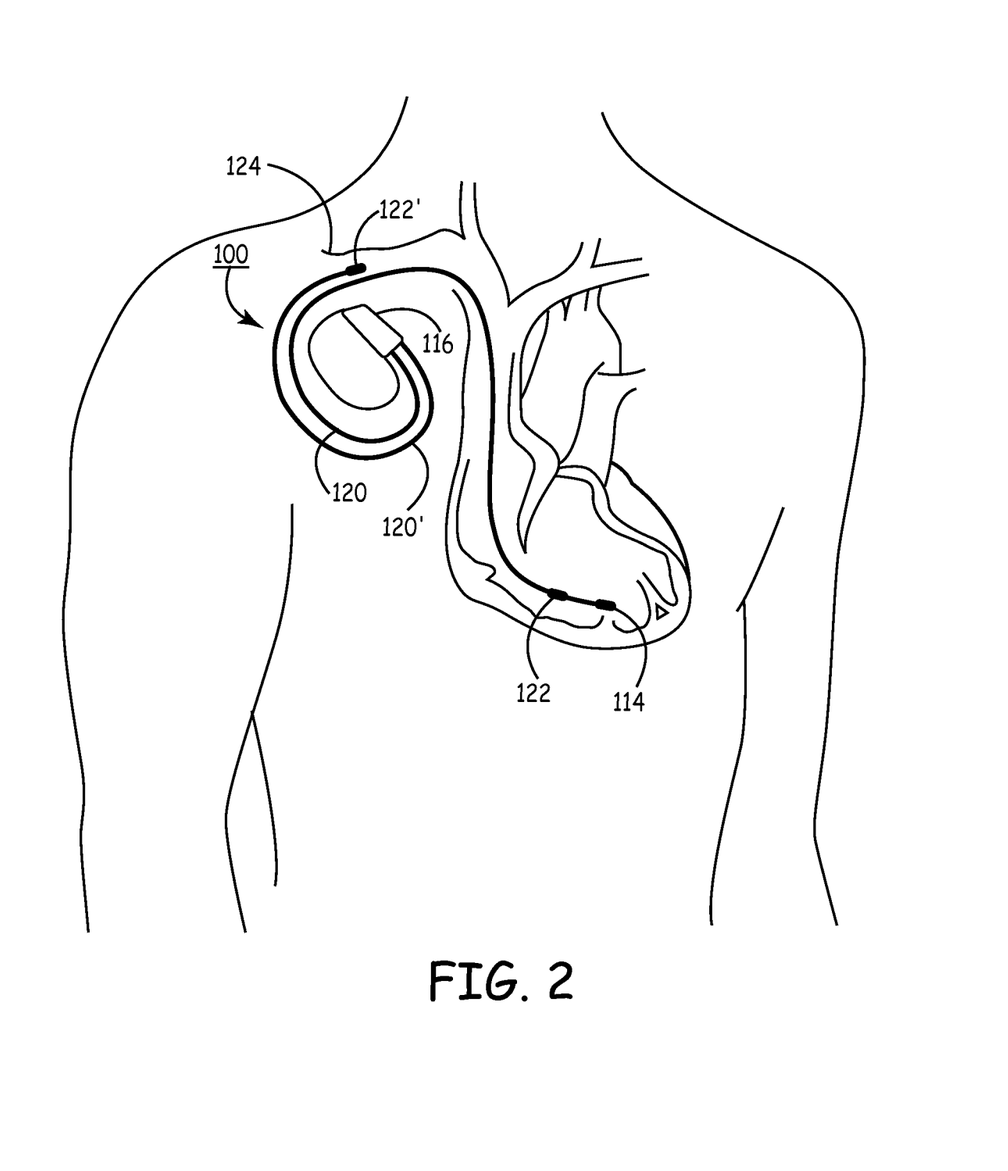
FIG. 2 is a schematic diagram of an alternative IMD system in which embodiments for predicting syncope may be implemented.

FIG. 2 is a schematic diagram of an alternative IMD system in which embodiments may be implemented. IMD 100 is shown coupled to a transvenous intracardiac lead 120 extending from IMD connector block 116. Lead 120 carries an electrode 114 for use in sensing an intracardiac EGM signal. Lead 120 additionally carries a sensor 122 for sensing a mechanical signal from which the cardiac ejection time can be derived. Sensor 122 may be, for example but not limited to, a pressure sensor, flow sensor, heart sound sensor, accelerometer, or impedance sensor. Sensor 122 is shown positioned within a heart chamber but could alternatively be advanced into an accessible arterial branch. Lead 120' is additionally shown coupled to IMD 100 as a tunneled lead extending toward an artery, within or outside the thoracic cavity, for positioning a sensor 122' in operative relation to an artery, such as right subclavian artery 124. Sensor 122' may be embodied as described above for detecting a pulsatile signal that varies with the pulsatile blood flow within the artery or the resultant pulsatile motion of the arterial wall. While embodiments described in conjunction with FIG. 1 are desirable for placement of a sensor relative to a peripheral artery and thereby eliminating the need to place transvenous or intrathoracic sensors, it is recognized embodiments of the invention are not limited to such extrathoracic placement. Sensors used for estimating cardiac ejection time may be positioned relative to any artery or heart chamber, not just peripheral arteries, and may be subcutaneous, submuscular, intrathoracic or intracardiac sensors.

Figure 3:
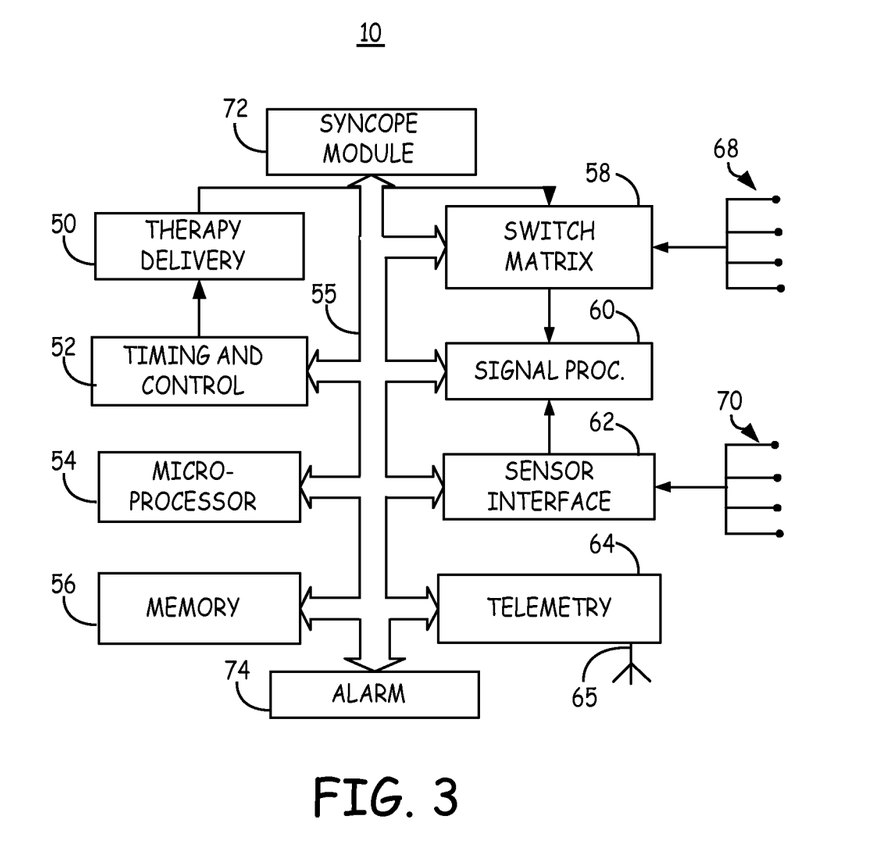
FIG. 3 is a functional block diagram of an IMD in which embodiments may be implemented, such as the IMD shown in FIG. 1.

FIG. 3 is a functional block diagram of an IMD in which embodiments may be implemented, such as IMD 10 shown in FIG. 1. IMD 10 generally includes timing and control circuitry 52 and an operating system that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55. IMD 10 may include a therapy delivery module 50 for delivering a therapy in response to determining a need for therapy based on sensed physiological signals. Therapy delivery module 50 may provide drug delivery therapies or electrical stimulation therapies, such as cardiac pacing, vagal nerve stimulation, or anti-arrhythmia therapies. Therapies are delivered by module 50 under the control of timing and control 52. When IMD is configured for delivering electrical stimulation therapies, module 50 is coupled to two or more electrodes 68 via an optional switch matrix 58. Switch matrix 58 may be used for selecting which electrodes and corresponding polarities are used for delivering electrical stimulation pulses. Electrodes 68 may correspond to a case electrode, electrodes 14 incorporated in IMD housing 12 (shown in FIG. 1) or other lead-based electrodes, including electrodes carried by lead 20 shown in FIG. 1, which may be tunneled subcutaneously, or a transvenous lead as shown in FIG. 2.

Electrodes 68 are also used for receiving cardiac electrical signals. Cardiac electrical signals may be monitored for use in diagnosing or monitoring a patient condition and may be used for determining when a therapy is needed and in controlling the timing and delivery of the therapy. When used for sensing, electrode 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac events. As will be described herein, IMD 10 senses ECG signals using electrodes 68 for measuring a QT interval in some embodiments of the invention.

IMD 10 is additionally coupled to one or more physiological sensors 70. Physiological sensors 70 may include pressure sensors, accelerometers, flow sensors, blood chemistry sensors, activity sensors, posture sensors or other physiological sensors known for use with implantable devices. Physiological sensors 70 may be carried by leads extending from IMD 10 or incorporated in or on the IMD housing 12. In particular, physiological sensors 70 include at least one sensor responsive to mechanical events corresponding to the onset and end of the cardiac ejection phase as described above.

Signals from sensors 70 are received by a sensor interface 62 which provides sensor signals to signal processing circuitry 60. Sensor signals are used by microprocessor 54 for detecting physiological events or conditions. In one embodiment, signals from a mechanical sensor responsive to an arterial pulse are received for determining an ejection time for use in predicting syncope. A syncope prediction module 72 may be implemented for receiving signals from sensor interface 62 or signal processor 60. Syncope prediction module 72 is configured to execute algorithms for determining a relative change in ejection time and/or a change in the ratio of ejection time to QT interval for predicting syncope as will be described herein. Data used in predicting syncope is provided to microprocessor 54 and may be stored in memory 56 for retrieval by a clinician.

In some embodiments, sensors 70 include a posture sensor. Syncope prediction module 72 receives a signal from the posture sensor, such as a 3-D accelerometer, for use in detecting a presyncope condition. Cardiac ejection time can change for many reasons, among them being postural changes of the patient. For example, when a patient moves from a supine to an upright position, the ejection time immediately decreases and reaches a new steady state corresponding to the new physical position. This change in ejection time is a normal physiological response to a postural change and not an indication of syncope. Thus, a posture sensor such as a 3D accelerometer can be used to monitor the patient's posture to discriminate a sudden change in ejection time due to posture change from a sudden change in ejection time associated with a presyncope condition. Methods for determining a patient posture in an implantable medical device are generally disclosed in U.S. Pat. No. 5,593,431 (Sheldon), hereby incorporated herein by reference in its entirety.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out upon receipt of a retrieval or interrogation instruction. A syncope monitoring algorithm may be stored in memory 56 and executed by microprocessor 54 with input received from electrodes 68 and sensors 70 for detecting a change in ejection time relative to QT intervals. Alternatively, syncope prediction module 72 may be embodied as dedicated circuitry for receiving and processing signals responsive to changes in ejection time. Microprocessor 54 may respond to the prediction of syncope by altering a therapy, triggering data storage, enabling other sensors for acquiring physiological data, or triggering alert 74 to generate an alert signal to the patient or a caregiver that syncope is predicted. Alert 74 may be an audible patient alarm, for example a piezoelectric transducer, an electrical stimulation for causing muscle twitching, a telemetry signal transmitted to an external device, or other signal perceptible by the patient.

IMD 10 further includes telemetry circuitry 64 and antenna 65. Programming commands or data are transmitted during uplink or downlink telemetry between ICD telemetry circuitry 64 and external telemetry circuitry included in a programmer or monitoring unit. Telemetry circuitry 64 and antenna 65 may correspond to telemetry systems known in the art.

Figure 4:
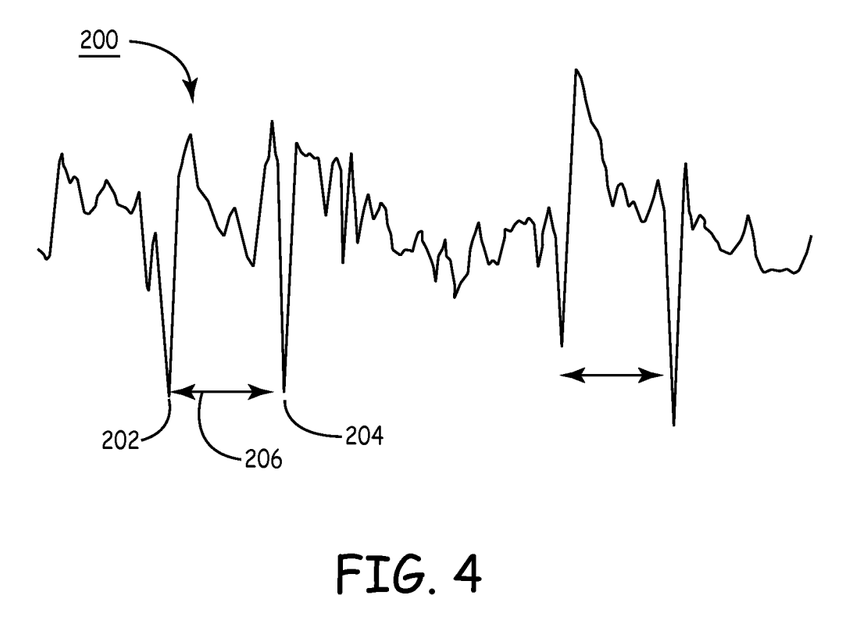
FIG. 4 is a sample recording of a signal obtained from an accelerometer positioned along a carotid artery.

FIG. 4 is a sample recording of a signal 200 obtained from an accelerometer positioned along a carotid artery. A first signal peak 202 caused by arterial wall motion occurs at a time corresponding to aortic valve opening. A second signal peak 204 caused by arterial wall motion occurs at a time corresponding to aortic valve closure. The time interval 206 between the first and second peaks 202 and 204 provides an estimate of cardiac ejection time. This measured ejection time 206 can be used for predicting syncope based on detecting a sudden change in ejection time 206. In one embodiment a moving average of the ejection time may be determined and newly measured ejection times 206 may be compared to the moving average. A syncope prediction criterion may then be defined as a predetermined number of consecutively measured ejection times 206 falling below a threshold defined as a percentage of or an absolute deviation from the moving average. It is recognized that numerous algorithms may be defined for detecting a sudden decrease in ejection time which generally include comparisons of one or more measured ejection times to a fixed threshold or previously measured ejection times.

Figure 5A:
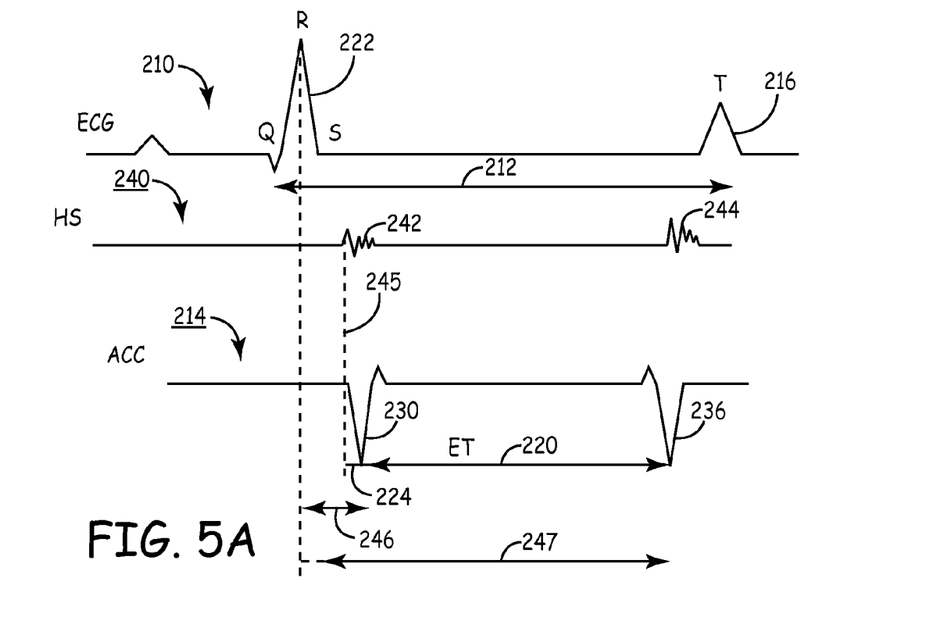
FIG. 5A is an illustration of an ECG signal, heart sound signal and arterial pulse signal during normal physiological conditions.

FIG. 5A is an illustration of an ECG signal, heart sound signal and arterial pulse signal during normal physiological conditions. ECG signal 210 includes a QRS complex 222 and a T-wave 216. A QT interval 212 is measured from the ECG signal 210 in some embodiments of the invention. As used herein, the "QT interval" refers to any interval measured from an ECG related signal that is correlated to the total time between depolarization and repolarization of the ventricle. As such, "QT interval" may actually be measured as the interval from a sensed R-wave peak to a sensed T-wave peak. In some embodiments, the QT interval may be measured from a ventricular pacing pulse to a sensed T-wave. Examples of QT interval monitoring methods are generally disclosed in U.S. Pat. No. 6,836,682 (van Dam), hereby incorporated herein by reference in its entirety.

Arterial pulse signal 214 is representative of the acceleration of a peripheral artery wall during normal physiological conditions. An ejection time 220 measured from acceleration signal 214, between first and second peaks 230 and 236, is slightly shorter than the QT interval 212 and will vary in direct relation to the QT interval 212 as heart rate changes under normal physiological conditions.

Heart sound signal 240 includes the first heart sound 242 corresponding to isovolumic contraction of the heart, starting with mitral valve closure and ending with aortic valve opening, and the second heart sound 244 corresponding to aortic valve closure and the end of ejection. The QRS complex 222 occurs just before the isovolumic contraction phase and the first heart sound 242, during which the mitral valve closes, the aortic valve opens and the ejection phase starts. The isovolumic contraction phase theoretically becomes shortened during a presyncopal condition due to reduced cardiac chamber filling occurring as a result of reduced blood pressure during neurologically-mediated syncope. On the other hand, isovolumic contraction time may theoretically increase during bradycardia-induced syncope. As such, an alternative or additional measurement for predicting syncope is a sudden change in the isovolumic contraction time, which may be estimated as a time interval 224 between the onset 245 of the first heart sound 242 and the first acceleration peak 230 of the arterial pulse signal 214.

A surrogate for the start of the first heart sound in estimating the isovolumic contraction time is the time from the QRS complex 222. As such, measuring a time interval for estimating the isovolumic contraction time could include detecting the R-wave of QRS complex 222 and measuring the time 246 until the first acceleration signal peak 224. An alternative measurement for use in predicting syncope is the time interval 247 from the onset 245 of the first heart sound 242, or as a surrogate the QRS complex 222, to the second peak 236 of the signal 214. This alternative time interval 247 will include changes in both the isovolumic contraction time and the ejection time.

Figure 5B:
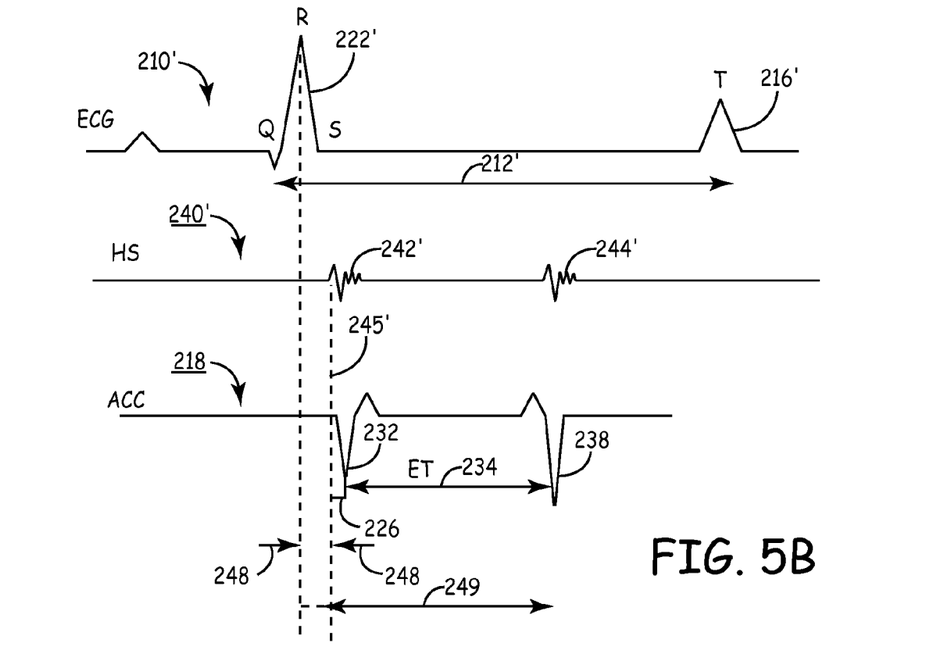
FIG. 5B is an illustration of an ECG signal, heart sound signal and arterial pulse signal during a presyncope condition.

FIG. 5B is an illustration of an ECG signal 210', heart sound signal 240' and arterial pulse signal 218 during a presyncope condition. ECG signal 210' includes a QRS complex 222' and a T-wave 216'. The QT interval 212' is similar to the normal physiological condition of FIG. 5A. However, due to a sudden drop in blood pressure, the isovolumic contraction time and the ejection time are shortened relative to the normal physiological conditions. As such, the interval 226 between the onset 245' of the first heart sound 242' and the first acceleration signal peak 232 is relatively shorter than the corresponding interval 224 shown in FIG. 5A. Likewise the time interval 248 between the R-wave and the first acceleration signal peak 232 is relatively shorter than the corresponding interval 246 shown in FIG. 5A. Similarly the ejection time 234 between the first peak 232 and the second peak 238 of acceleration signal 218 is shorter compared to the ejection time 220 shown in FIG. 5A. As such, the overall interval 249, which includes changes in both the isovolumic contraction time and the ejection time, is also shorter than the corresponding interval 247 shown in FIG. 5A.

The second accelerometer signal 218 is representative of the acceleration signal of a peripheral artery during a presyncopal condition associated with neurologically-mediated syncope. Cardiac filling is reduced prior to syncope resulting in the shortened ejection time 234, even when the heart rate and QT interval 212 are relatively unchanged. A normal ratio of the ejection time to the QT interval, as shown in FIG. 5A, might be about 0.8 (note the illustrated signals may not be drawn exactly to scale). Just prior to syncope, this ratio may suddenly decrease to about 0.6 to 0.7. As such, the ratio of ejection time to QT interval may be compared to a fixed threshold or to a predetermined moving average to detect a sudden decrease indicative of syncope.

In some cases, syncope is preceded by a sudden drop in heart rate, with or without a drop in blood pressure. As such, a sudden increase in ejection time may occur that is disproportional to the more slowly-occurring change in the QT interval that accompanies the sudden drop in heart rate. Thus it is recognized that a sudden decrease of the ratio of ejection time to QT interval, as described above, may be one predictor of syncope, and a sudden increase of the same ratio, for example an increase from about 0.8 to about 0.9, may be another predictor of syncope. As will be further described below, an increase in QT interval associated with a sudden drop in heart rate may lag the heart rate change and the ejection time increase. As such, a sudden increase in ejection time may occur with or without a change in the ratio of the ejection time to the QT interval depending on the time frame of the measurements and the response characteristics of the QT interval changes. In general, both a sudden increase and a sudden decrease in any of the intervals 220, 224, 246 and 247 shown in FIG. 5A can indicate impending syncope.

Figure 6:
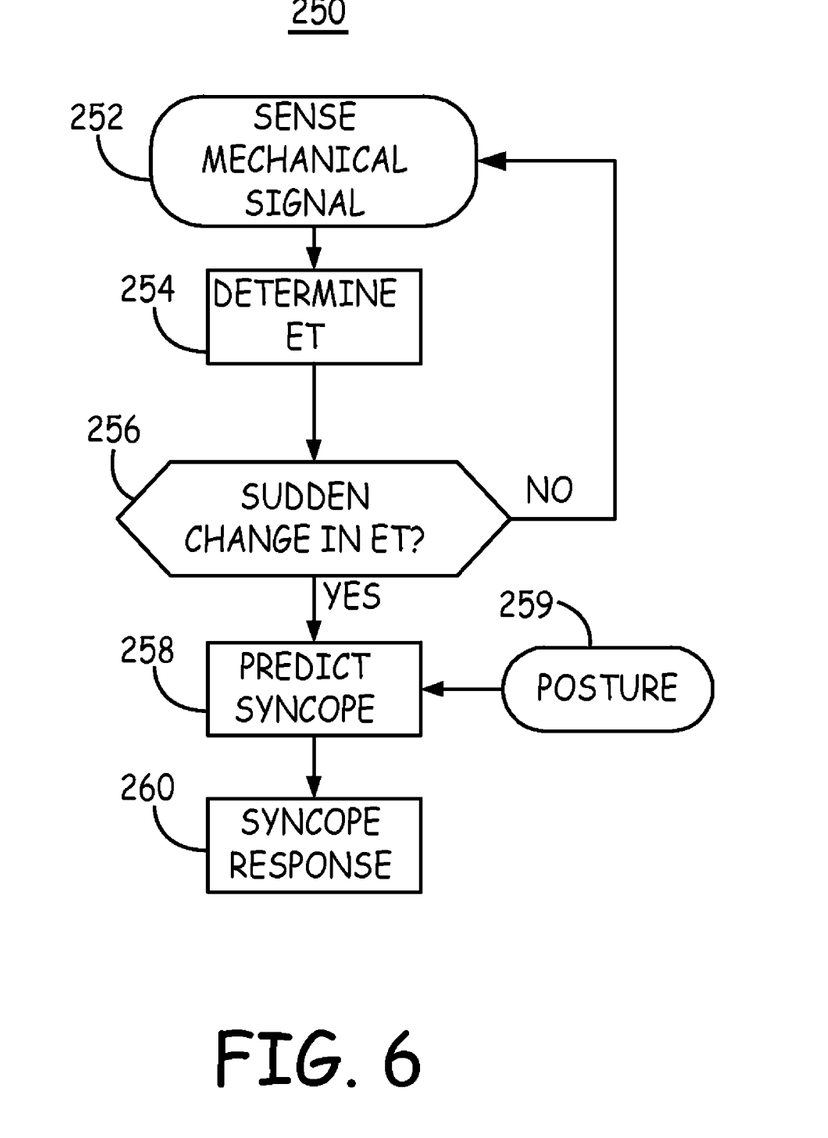
FIG. 6 is a flow chart of a method for predicting syncope according to one embodiment.

FIG. 6 is a flow chart of a method 250 for predicting syncope according to one embodiment. Flow chart 250 is intended to illustrate the functional operation of the device, and should not be construed as reflective of a specific form of software or hardware required. It is believed that the particular form of software will be determined primarily by the particular system architecture employed in the device and by the particular sensing and therapy delivery methodologies employed by the device.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 252, at least one signal is sensed that is responsive to mechanical events associated with the cardiac ejection phase. As described above, the signal may be an accelerometer signal or other motion sensor signal responsive to arterial wall motion. The signal may alternatively be a flow signal responsive to the arterial blood flow pulsatility. Other mechanical signals include acoustical signals for sensing heart sounds and impedance sensors for sensing heart chamber or blood vessel volumes. Using the mechanical signal, ejection time (ET) is determined at block 254 by detecting a signal event corresponding to the onset of the ejection phase and a second signal event corresponding to the end of the ejection phase.

At block 256, the ejection time is compared to a previous ejection time measurement, a previously determined average ejection time, or a predefined threshold. If a sudden change in ejection time is detected, which may be a sudden increase or a sudden decrease, as determined at block 256, the sudden change is used in predicting syncope at block 258. The change in ET may be used alone as a predictor of syncope or in combination with QT interval changes, as will be described below, or in combination with posture changes 259, or other related parameters.

Syncope prediction may take into account changes in patient posture 259. For example, if the sudden change in ejection time is coincident with a change in patient posture, syncope may not be predicted. In the absence of any change in patient posture, syncope is predicted in response to a sudden change in ejection time. At block 260 a syncope response is provided when syncope is predicted. The response provided at block 260 may include generating a patient alert, initiating or adjusting a therapy, storing data, triggering other sensor signal data acquisition, or the like.

Other time intervals may be measured and substituted for, or used in combination with, the ejection time in method 250. Other time intervals include an estimated isovolumic contraction time measured as an interval between the onset of a first heart sound and the first acceleration peak of an arterial pulse signal, a surrogate for the estimated isovolumic contraction time measured as an interval between the QRS complex and the first acceleration peak of an arterial pulse signal, or an estimate of the combined isovolumic and ejection phases measured as the interval between either the onset of the first heart sound or the QRS complex and the second acceleration peak of an arterial pulse signal. The measurement of each of these intervals is described above in conjunction with FIGS. 5A and 5B. A sudden change in any of these intervals, or combination of these intervals, may be used as a predictor of syncope.

Figure 7:
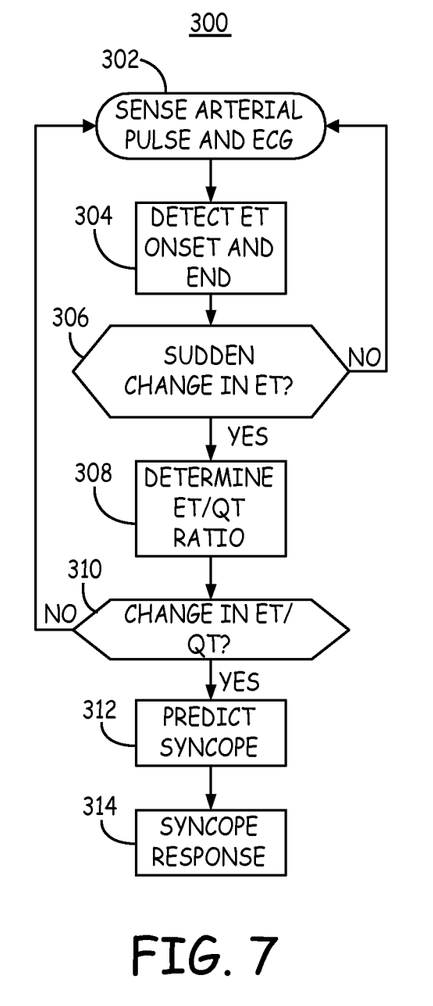
FIG. 7 is a flow chart of a method for predicting syncope based on ejection time measured from an arterial pulse signal.

FIG. 7 is a flow chart of a method 300 for predicting syncope based on ejection time measured from an arterial pulse signal. An arterial pulse signal is measured at block 302 using an accelerometer positioned along a peripheral artery. An ECG signal is also measured at block 302, using, for example, subcutaneous sensing electrodes. At block 304, events corresponding to the onset and end of the cardiac ejection time (ET) are detected from the arterial pulse signal, as described above in conjunction with FIG. 4. The ejection time may be determined on a beat-by-beat or less frequent basis. At block 306, an ejection time measured between the events detected at block 304 is compared to a threshold for detecting a sudden change in ejection time. The threshold may be a predefined fixed threshold or defined as a function of one or more previously measured ejection times. Since ejection time will normally fluctuate with heart rate, the threshold may be defined as a function of heart rate in some embodiments.

If a change in ejection time is detected, the QT interval is measured and the ratio of the ejection time and the QT interval is determined at block 308. As such, in one embodiment, a change in ejection time is first detected then the QT interval measurement is performed to determine a ratio of ejection time to QT interval (ET/QT) for the same or subsequent heart beats. Alternatively, block 306 may be omitted and the ratio of ejection time to QT interval may be determined directly at block 308. The ratio of ejection time to QT interval is compared to a threshold at block 310 to determine if a change indicative of syncope is detected. The threshold may be a predefined fixed threshold or defined as a function of one or more previously measured ratios of ejection time to QT interval.

If a sudden change in the ratio is detected at block 310, syncope is predicted at block 312. In one embodiment, a sudden change in the ratio is a change of at least about 10% occurring within about 20 to 120 seconds. As described above, other factors may be relied upon for predicting syncope at block 312, including, for example, patient posture or any of the other time intervals described in conjunction with FIGS. 5A and 5B. Upon predicting syncope, a syncope response is provided at block 314 as described above in conjunction with FIG. 6. Thus method 300 enables the device to predict syncope and provide a patient alert or other response without measuring or determining blood pressure and without necessarily determining an actual heart rate.

Figure 8:
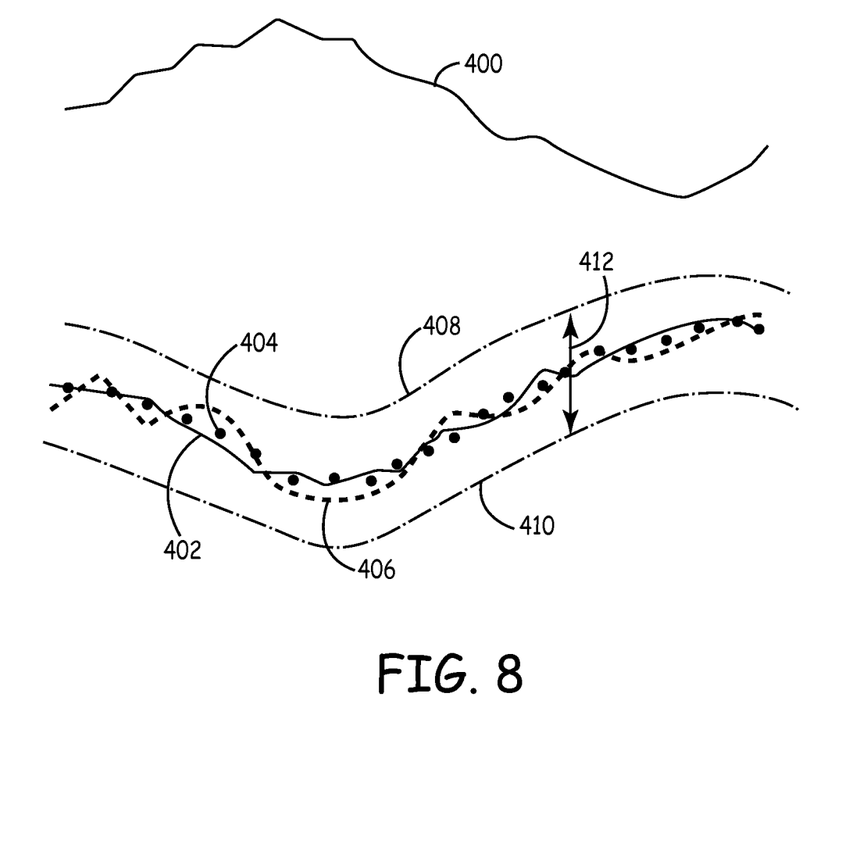
FIG. 8 depicts a recording of heart rate, QT interval (solid line), a running average of QT interval (dotted line), and ejection time (dashed line) under normal physiological conditions.

FIG. 8 depicts a recording of heart rate 400, QT interval 402 (solid line) and ejection time 406 (dashed line) under normal physiological conditions. As heart rate 400 fluctuates over a time period of several minutes, the QT interval 402 fluctuates in a similar manner but slightly lagging the changes in heart rate 400. The QT interval changes might lag changes in heart rate by about 30 to 60 seconds. A running average of the QT interval 404 is shown by a dotted line. The running average 404 may be computed, for example, as the average of the previous eight consecutively measured QT intervals. An upper physiological limit 408 and a lower physiological limit 410 are defined based on the QT interval running average 404. The upper and lower limits 408 and 410, respectively, define a physiological bandwidth 412 within which the QT interval 402 and ejection time 406 are expected to remain during normal physiological conditions. The upper and lower limits 408 and 410 may be defined such that an area of the bandwidth 412 is the same above and below the QT interval running average 404, or limits 408 and 410 may be defined to result in a non-symmetrical bandwidth 4120 about the QT interval running average 404.

Figure 9:
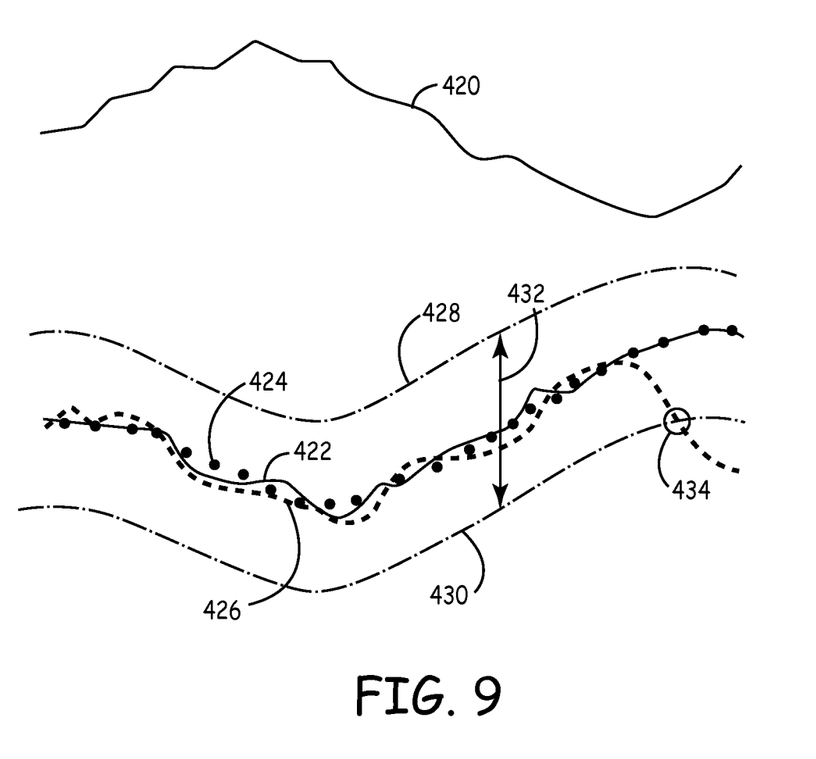
FIG. 9 depicts heart rate, QT interval, a running average of QT interval, and ejection time during an interval of time preceding neurologically-mediated syncope.

FIG. 9 depicts heart rate 420, QT interval 422, a running average of QT interval 424, and ejection time 426 during an interval of time preceding neurologically-mediated syncope. A physiological bandwidth 432 is defined by upper and lower limits 428 and 430, respectively, which are based on the running QT interval average 424. In the situation shown, a sudden drop in blood pressure causes the ejection time 426 (dashed line) to suddenly decrease without a corresponding change in QT interval 422 (solid line). At time point 434, the ejection time 426 crosses a defined lower limit 430 of physiological bandwidth 432. This drop in ejection time 426 occurs despite a relatively stable heart rate 420 and QT interval 422. Accordingly, at time point 434, syncope may be predicted. It is recognized that the ejection time 426 may also be averaged to eliminate the effect of single point outliers. However if a running average of ejection time 426 is tracked, it is computed using just a few measurements, for example three consecutive measurements, to allow sudden changes in ejection time to be quickly detected.

Figure 10:
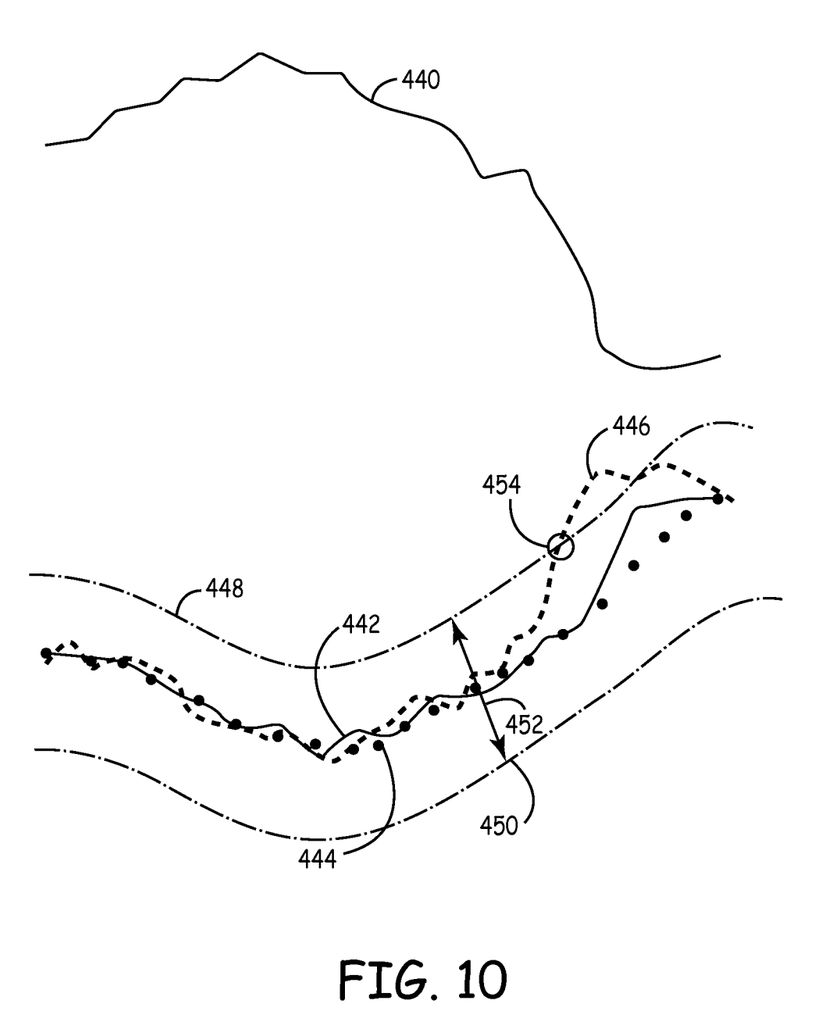
FIG. 10 depicts heart rate, QT interval, a running average of the QT interval, and ejection time during an interval of time preceding bradycardia-induced syncope.

FIG. 10 depicts heart rate 440, QT interval 442, a running average of the QT interval 444, and ejection time 446 during an interval of time preceding bradycardia-induced syncope. Heart rate 440 is seen to decrease dramatically. The change in QT interval 442 (solid line) lags the change in heart rate 440. The ejection time 446 (dashed line) suddenly increases with the decrease in heart rate 440 in response to the longer filling times of the ventricles. A QT interval running average 444 (dotted line) is used to set upper and lower limits 448 and 450 of a physiological bandwidth 452 defining normal physiological fluctuations for the QT interval 442 and ejection time 446. The ejection time 446 crosses the upper limit 448 at time point 454. Syncope may be predicted at this time point 454 in response to the sudden increase in ejection time 446.

Figure 11:
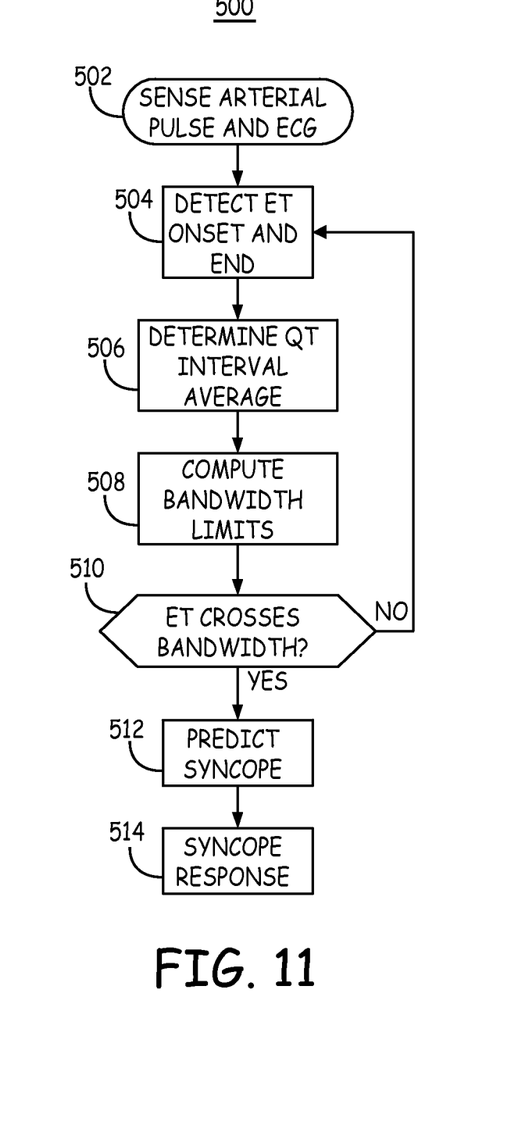
FIG. 11 is a flow chart of an alternative method for predicting syncope.

FIG. 11 is a flow chart of an alternative method 500 for predicting syncope based on defining a physiological bandwidth for ejection time. At block 502, a signal responsive to the arterial pulse is sensed for estimating ejection time. An ECG signal is sensed for estimating the QT interval. At block 504, an onset and end point of the ejection time are detected from the arterial pulse signal. The ejection time may be averaged with previous measurements to determine a short term running average, for example over the last two to five heart beats.

At block 506, QT interval measurements are averaged, for example over the last six to twelve beats. Using the running average of the QT interval, upper and lower limits of a physiological bandwidth for the ejection time is defined. The upper and lower limits may be defined as a percentage of the running QT interval average. For example, an upper limit may be set at about 105% to 115% of the running QT interval average, and a lower limit set at about 85% to 95% of the running average. If the measured ejection time, or a short term running average of the measured ejection time, crosses either the upper or lower limit of the physiological bandwidth, as determined at block 510, syncope is predicted at block 512. A syncope response is provided at block 514 which will generally include generating a patient alert.

Thus, systems and methods for predicting syncope have been presented in the foregoing description with reference to specific embodiments. It is appreciated that various modifications to the referenced embodiments may be made without departing from the scope of the invention as set forth in the following claims.

The invention claimed is:

1. A method for predicting syncope for use in an implantable medical device, comprising:
sensing a physiological signal;
determining a time interval corresponding to cardiac ejection time from the physiological signal;
detecting a change in the time interval;
predicting syncope in response to the detected change; and
generating a patient alert in response to the predicted syncope.

2. The method of claim 1, wherein sensing the physiological signal comprises sensing a signal responsive to an arterial pulse.

3. The method of claim 2 wherein sensing the signal comprises sensing a motion of an arterial wall.

4. The method of claim 3 wherein determining the time interval comprises detecting a first acceleration signal corresponding to aortic valve opening and detecting a second acceleration signal corresponding to aortic valve closure.

5. The method of claim 4 further comprising:
sensing an ECG signal;
determining a QT interval from the ECG signal;
determining a ratio of the time interval to the QT interval; and
wherein detecting a change in the time interval comprises detecting a change in the ratio of the time interval to the QT interval.

6. The method of claim 4 further comprising:
sensing a signal corresponding to an onset of an isovolumic contraction of the heart;
determining a second time interval beginning at a time corresponding to the onset of the isovolumic contraction of the heart;
detecting a change in the second time interval; and
predicting syncope in response to the detected change in the second time interval.

7. The method of claim 6 wherein sensing the signal corresponding to an onset of isovolumic contraction comprises one of sensing a QRS complex and a first heart sound.

8. The method of claim 7 wherein the second time interval ends at a time corresponding to one of the first acceleration signal and the second acceleration signal.

9. The method of claim 1 wherein detecting the change in the time interval comprises detecting a change occurring in less than about two minutes.

10. The method of claim 1 further comprising:
sensing a signal responsive to changes in a patient posture;
wherein predicting syncope comprises predicting syncope in response to the detected change in the time interval when a patient posture change is absent.

11. The method of claim 1 further comprising:
sensing an ECG signal;
determining a QT interval from the ECG signal;
determining a physiological limit in response to the QT interval;
wherein detecting a change in the time interval comprises detecting the time interval crossing the physiological limit.

12. An implantable medical device system for predicting syncope, comprising:
a sensor for sensing a physiological signal;
a processor configured to receive the sensor signal, determine a time interval corresponding to a cardiac ejection time from the physiological signal, detect a change in the time interval, and predict syncope in response to the detected change in the time interval; and
a patient alert module for generating a patient alert in response to the predicted syncope.

13. The device of claim 12, wherein the sensor comprises a sensor responsive to an arterial pulse.

14. The device of claim 13 wherein the sensor comprises an accelerometer sensitive to motion of an arterial wall.

15. The device of claim 14 wherein the processor determining the time interval detects a first acceleration signal corresponding to aortic valve opening and detects a second acceleration signal corresponding to aortic valve closure.

16. The device of claim 15 further comprising:
an electrode for sensing an ECG signal;
wherein the processor receives the ECG signal and determines a QT interval from the ECG signal, determines a ratio of the time interval to the QT interval, detects a change in the ratio of time interval to the QT interval, and predicts syncope in response to the detected changed ratio.

17. The device of claim 15 further comprising:
a sensor for sensing a signal corresponding to an onset of isovolumic contraction of the heart,
the processor further configured to determine a second time interval beginning at a time corresponding to the onset of isovolumic contraction of the heart, detect a change in the second time interval, and predict syncope in response to the detected change in the second time interval.

18. The device of claim 17 wherein the sensor for sensing a signal corresponding to an onset of isovolumic contraction comprises one of an ECG sensing electrode and an acoustical sensor responsive to the first heart sound.

19. The device of claim 18 wherein the second time interval ends at a time corresponding to one of the first acceleration signal and the second acceleration signal.

20. The device of claim 12 further comprising:
a sensor responsive to changes in patient posture;
the processor further configured to detect a change in patient posture and predict syncope in response to the detected change in the time interval when a patient posture change is absent.

21. The device of claim 12 further comprising:
an electrode for sensing an ECG signal;
wherein the processor is further configured to determine a QT interval from the ECG signal, determine a physiological limit in response to the QT interval, and detect a crossing of the physiological limit by the time interval as a change in the time interval.

22. The device of claim 12 wherein the processor detects the change in the time interval by detecting a change occurring in up to about two minutes.

23. A non-transitory computer readable medium for storing a set of instructions for predicting syncope, which, when implemented in an implantable medical device system, cause the system to:
sense a physiological signal;
detect a time interval corresponding to cardiac ejection time from the physiological signal;
detect a change in the time interval;
predict syncope in response to the changed time interval; and
generate a patient alert in response to the predicted syncope.

* * * * *